United States Patent
Stone et al.

(10) Patent No.: US 7,674,276 B2
(45) Date of Patent: Mar. 9, 2010

(54) ROTATIONAL SECURING OF A SUTURE

(75) Inventors: Kevin T Stone, Winona Lake, IN (US);
Gregory J Denham, Warsaw, IN (US);
Julie L Sauer, Madison, WI (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 494 days.

(21) Appl. No.: 11/545,036

(22) Filed: Oct. 6, 2006

(65) Prior Publication Data

US 2008/0086138 A1 Apr. 10, 2008

(51) Int. Cl.
*A61B 17/04* (2006.01)

(52) U.S. Cl. .................. 606/232; 606/300; 606/103; 606/74; 411/396; 411/391; 411/383; 24/135 N (58) Field of Classification Search .......... 606/232, 606/300, 103, 74; 411/396–391, 383; 24/135 N
See application file for complete search history.

(56) References Cited

U.S. PATENT DOCUMENTS

| | | | |
|---|---|---|---|
| 4,512,346 A | 4/1985 | Lemole | |
| 4,750,492 A | 6/1988 | Jacobs | |
| 4,870,957 A * | 10/1989 | Goble et al. | 623/13.12 |
| 5,152,790 A * | 10/1992 | Rosenberg et al. | 623/13.14 |
| 5,263,803 A * | 11/1993 | Anquetin | 411/31 |
| 5,370,662 A * | 12/1994 | Stone et al. | 606/232 |
| 5,383,905 A | 1/1995 | Golds et al. | |
| 5,443,482 A * | 8/1995 | Stone et al. | 606/232 |
| 5,458,601 A * | 10/1995 | Young et al. | 606/232 |
| 5,486,197 A * | 1/1996 | Le et al. | 606/232 |
| 5,501,688 A | 3/1996 | Whiteside et al. | |
| 5,584,835 A * | 12/1996 | Greenfield | 606/232 |
| 5,630,824 A | 5/1997 | Hart | |
| 5,919,208 A | 7/1999 | Valenti | |
| 5,957,953 A * | 9/1999 | DiPoto et al. | 606/232 |
| 6,066,160 A | 5/2000 | Colvin et al. | |
| 6,086,608 A | 7/2000 | Ek et al. | |
| 6,126,677 A | 10/2000 | Ganaja et al. | |
| 6,200,329 B1 | 3/2001 | Fung et al. | |
| 6,293,961 B2 | 9/2001 | Schwartz et al. | |
| 6,361,258 B1 * | 3/2002 | Heesch | 411/178 |
| 6,520,980 B1 | 2/2003 | Foerster | |
| 6,616,694 B1 * | 9/2003 | Hart | 623/13.14 |
| 6,666,877 B2 * | 12/2003 | Morgan et al. | 606/232 |
| 7,144,413 B2 * | 12/2006 | Wilford et al. | 606/232 |
| 7,416,556 B2 * | 8/2008 | Jackson | 606/232 |
| 2002/0156476 A1 * | 10/2002 | Wilford | 606/72 |
| 2003/0004545 A1 * | 1/2003 | Burkhart et al. | 606/232 |

(Continued)

OTHER PUBLICATIONS

Arthrex, Inc., Arthrex PushLock™ Knotless Anchor for Bankart and SLAP Repair, 2006.

*Primary Examiner*—(Jackie) Tan-Uyen T. Ho
*Assistant Examiner*—Son Dang
(74) *Attorney, Agent, or Firm*—Harness, Dickey (57) ABSTRACT

A suture fixation apparatus having a first body portion having a bone engaging feature to fixedly engage a bony tissue and a second body portion defining an eyelet for receipt of a suture. The second body portion is rotatable with respect to the first body portion. Rotating the second body portion causes the suture to form a twist to frictionally secure the suture.

18 Claims, 8 Drawing Sheets

U.S. PATENT DOCUMENTS

| | | |
|---|---|---|
| 2004/0098050 A1 | 5/2004 | Roerster et al. |
| 2004/0098052 A1 | 5/2004 | West, Jr. et al. |
| 2004/0133239 A1 | 7/2004 | Singhatat |
| 2004/0138706 A1 | 7/2004 | Abrams et al. |
| 2005/0055052 A1 | 3/2005 | Lombardo et al. |
| 2005/0090827 A1* | 4/2005 | Gedebou .................. 606/72 |
| 2005/0131430 A1 | 6/2005 | Ravikumar |
| 2005/0149120 A1 | 7/2005 | Collier et al. |
| 2008/0015509 A1* | 1/2008 | Backman et al. ............ 604/174 |

* cited by examiner

ROTATIONAL SECURING OF A SUTURE

FIELD

The present disclosure relates to methods and apparatuses for securing a suture. In particular, the present disclosure relates to rotational securing of a suture using a suture anchor.

BACKGROUND

The statements in this section merely provide background information related to the present disclosure and may not constitute prior art.

Surgical or medical procedures are often performed on a body, for example a human body or anatomy, to repair or replace various portions thereof. For example, the soft tissues of the body may need to be reattached to bones due to trauma, overuse, surgical intervention, or disease.

Soft tissue can be reattached to bone using devices such as screws, staples, and various types of suture anchors. Soft tissues are often fixed to various positions on the bone. For example, to replace a natural tendon fixation point or to replace the tendon itself, fixing a graft to a selected bone area may be desired. One means to fix the soft tissue to the selected area is to provide a suture through a selected portion of the soft tissue and fix the other end of the suture to a selected area on the bone. Various structures can be provided to anchor or hold the suture in the selected bone area. To secure the sutures, the free ends of the suture are tied together to form a knot.

The use of knots in surgical procedures, however, can be improved upon. First, in minimally invasive procedures, such as arthroscopic or laparoscopic procedures, the surgical site is not readily accessible and limits the surgeon's ability to tie a knot manually and the site must be secured remotely. One remote method of securing the suture is tying each of the suture ends into a knot extracorporeally and then remotely advancing the knot into the surgical site using suitably configured instruments. Securing the suture remotely can be cumbersome and time consuming.

Second, knots may create stress points in a suture on opposite sides of the knot. When a failure load is applied to a knotted suture, the suture may break at the knot, even though the suture is otherwise free from imperfections.

Accordingly, there is a need for improved devices for securing a suture without a knot. There is a need for surgical methods to facilitate easy and efficient securing of the suture.

SUMMARY

The present teachings provide a suture fixation apparatus comprising a first body portion having a bone engaging feature to fixedly engage a bony tissue and a second body portion defining an eyelet for receipt of a suture where engaging the second body portion rotates the eyelet with respect to the first body portion. Rotating the second body portion causes the suture to form a twist to frictionally secure the suture. The suture fixation apparatus can be a suture anchor.

The first body portion can include a suture receiving opening in communication with the eyelet. The first body portion can define a recess. The recess can include a clearance to accommodate the twist in the suture.

The second body portion can be located at the proximal end of the suture fixation apparatus. The second body portion can be at least partially contained in the recess or the second body portion can be fully contained in the recess. The second body portion can be contained in the recess such that a proximal end of the second body portion and a proximal end of the first body portion are substantially flush.

The suture fixation apparatus can include a drive end to receive a driver. The drive end can be used to advance the suture anchor by impacting, screwing, or pushing the suture anchor.

The suture fixation apparatus can include a ratcheting mechanism to provide one-directional movement of the second body portion with respect to the first body portion. The ratcheting mechanism can include at least one ridge, located on one of the first body portion and said second body portion and at least one pawl disposed opposite the ridge located on the other of the first body portion and the second body portion. The suture fixation apparatus can include a plurality of ridges and a plurality of pawls.

The present teachings also provide a suture fixation apparatus comprising a first body portion having a first suture receiving channel and a second body portion having a second suture receiving channel. Aligning the first suture receiving channel and the second suture receiving channel into an open position provides a continuous passage for movement of a suture therebetween. Rotating the first suture receiving channel with respect to the second suture receiving channel misaligns the first suture receiving channel and the second suture receiving channel to prevent movement of the suture therebetween. The suture receiving channel can be formed at a central axis of the suture fixation apparatus.

The suture fixation apparatus can also include an interface where a first mating surface of the first body portion engages a second mating surface of the second body portion. The first mating surface can include a first threaded region having a first thread and the second mating surface can include a second threaded region having a second thread mated to the first thread. Engaging the first threaded region and the second threaded region moves the suture anchor into a deployed position and lodges the suture between the first mating surface and the second mating surface. The first body portion threaded region and the second body threaded region can be offset from the suture receiving channel.

The present teachings also provide a suture fixation apparatus, comprising a threaded suture anchor body to fixedly engage a bony tissue where the suture anchor body has a proximal end and a distal end; and a rotatable base having an eyelet where the rotatable base and the eyelet are located on an interior region of the threaded suture anchor body and are distal to the suture anchor body proximal end. Rotation of the rotatable base causes the suture to form a twist to frictionally secure the suture The continuous suture receiving channel can be aligned along the transverse axis of the suture anchor or the longitudinal axis of the suture anchor. The first body portion can comprise an eyelet.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. Although certain examples and surgical methods disclosed herein are in conjunction with a suture anchor, it is understood that the suture fixation device can be any device with which to hold a suture.

Referring to FIGS. 1 through 9B, a suture fixation apparatus 10 is provided. A first body portion 12 for engaging bone is located at the distal end of the suture fixation apparatus 10. A second body portion 14 is located proximally to the first body portion 12. The second body portion 14 comprises an eyelet 16 for a suture 18. The second body 14 portion is rotatable with respect to the first body portion 12. Rotating the second body 14 portion causes the suture 18 to fold on itself to form a twist T which frictionally secures the suture. The twist T advantageously prevents applying compressive forces from the fixation apparatus 10 onto the suture 18.

Figure 1:
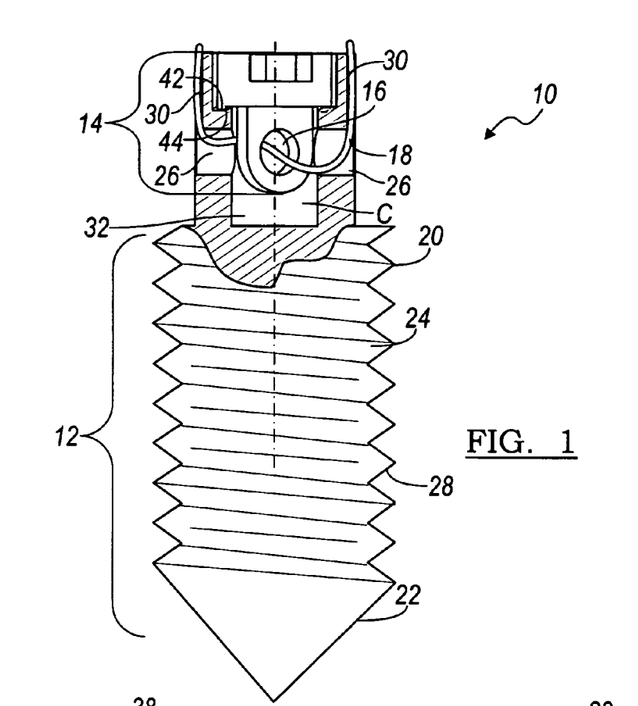
FIG. 1 depicts a suture anchor having a rotatable eyelet according to various embodiments.
Figure 2:
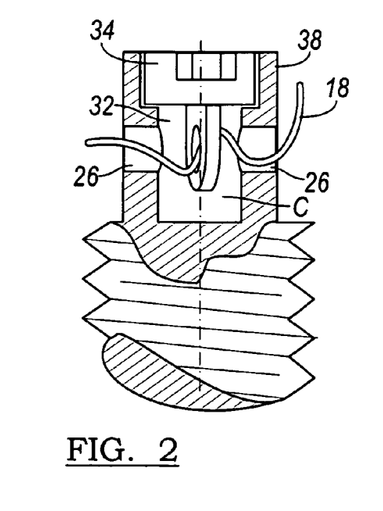
FIG. 2 depicts a partially rotated eyelet according to various embodiments.

In various embodiments, the first body portion 12 can be a suture anchor 20 to engage bone. The suture anchor 20 includes a tip 22, an anchor body shaft 24, and at least one suture receiving opening 26. The tip 22 is located at the distal end of the first body portion 12. The tip 22 can be formed to substantially ease entry of the anchor 20 into a bony region or can be formed to allow the anchor 20 to be substantially self-drilling or self-tapping. Therefore, the tip 22 can be round or bullet nose, square, substantially sharp, or any other appropriate design to allow for entry of the suture anchor 20 into a selected bony portion.

The anchor body shaft 24 is located proximal to the tip 22. The anchor body shaft 24 can include an attachment feature to engage bone and fixedly hold the first body portion 12 in bone. As shown, the attachment feature includes threads 28. It is understood that other attachment features can be used such as one or several of a spike, pin, ridge, tooth, or another bone engaging element to fixedly hold the anchor body shaft 24. Various combinations of attachment features can also be used.

The threads 28 can be designed in any appropriate fashion. Non-limiting examples of threads 28 include helical threads, threads with parallel angled surfaces, or annular ridges. The threads 28 generally begin at the distal end of the anchor body shaft 24 end at the proximal end of the anchor body shaft 24. The threads 28 can be provided in a continuous or discontinuous pitch. The threads 28 can also be limited to only a region of the anchor body shaft 24. In some embodiments, the thread pattern can begin on the tip 22 and continue along the anchor body shaft 24.

The suture receiving openings 26 are located at the proximal end of the anchor body shaft 24. The suture receiving openings 26 are defined by the first body portion 12 and are adapted for passage of a single suture 18 strand or multiple suture 18 strands. The suture receiving openings 26 are in communication with the eyelet 16 of the second body portion 12. The suture receiving openings 26 and the eyelet 16 can form a continuous pathway along the transverse axis of the suture anchor 20 through which the suture 18 can pass.

Suture 18 passes through the first suture receiving opening 26, through the eyelet 16, and through the opposing suture receiving opening 26. The suture receiving openings 26 can be aligned with the eyelet 16 in substantially the same horizontal plane as depicted in FIG. 1, or the suture receiving opening 26 can be lower or higher than the eyelet 16. The continuous pathway formed by the suture receiving openings 26 and the eyelet 16 can be curved or angled to accommodate differences in the vertical location of the eyelet 16 with respect to the suture receiving openings 26. As described later herein, the suture receiving openings 26 can also be formed as part of the drive end of the suture anchor 20. In various embodiments, it is desirable to have the suture receiving openings 26 adjacent to a channel 30 in the first anchor body 12. The channel 30 can be used to guide a suture 18 along the proximal end of the suture anchor 20.

The first body portion 12 includes an opening or recess 32 for the second body portion 14. The opening or recess 32 can be located at or near the proximal end of the anchor body shaft 24. The opening or recess 32 is sized to allow the corresponding element of the second body portion 14 to rotate therein (or thereon) to form the twist T in the suture 18. The opening or recess 32 provides sufficient clearance space C for the twist T.

The second body portion 14 defines the eyelet 16. The eyelet 16 is adapted to allow the suture 18 to pass therethrough. The eyelet 16 is in communication with the suture receiving openings 26 in the first body portion 12. The eyelet 16 can be of any suitable size or shape and can allow for the passage of a single suture, folded or looped suture, or multiple sutures. The suture receiving openings 26 can also be appropriately shaped or sized to allow for passage of a single suture, folded or looped suture, or multiple sutures. The eyelet 16 is sized to allow complete rotation of the second body portion 14, particularly the eyelet 16 within its containing structure.

Figure 4:
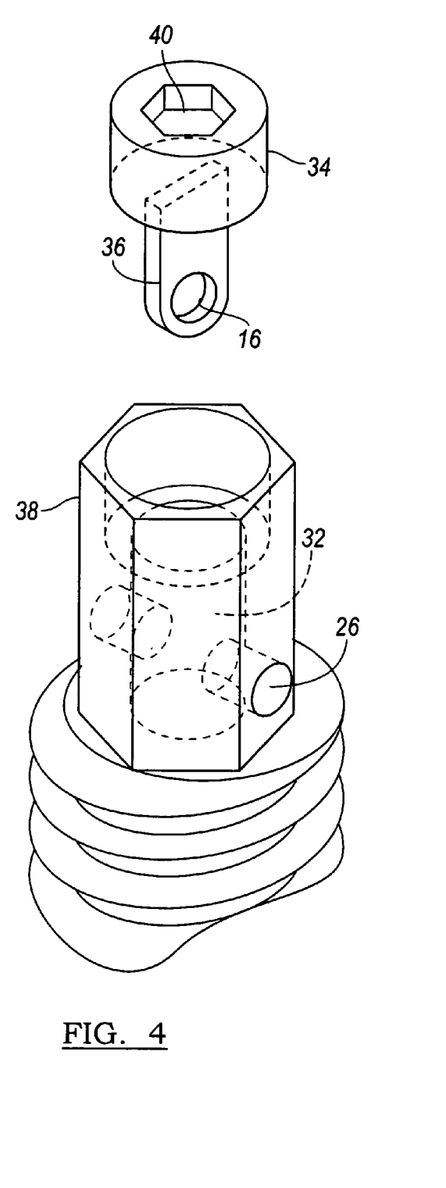
FIG. 4 depicts a rotatable eyelet having a female hex end and a corresponding suture anchor according to various embodiments.
Figure 7:
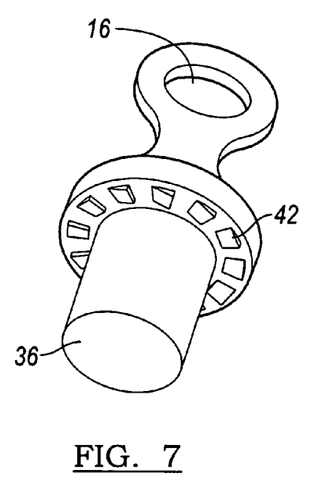
FIG. 7 depicts a rotatable eyelet with ratcheting elements to produce one-way rotation of the eyelet according to various embodiments.

The second body portion 14 also includes a rotation base 34 to facilitate rotation of the second body portion 14 and the eyelet 16. The rotation base 34 fits in (or on) the opening 32 of the first body portion 12 and allows for 360° of movement of the second body portion 14 with respect to the first body portion. The rotation base 34 can include an arm 36 adapted to fit at the opening 32 of the first body portion 12. The arm 36 can be distal to the eyelet 16, as shown in FIG. 7, or the arm 36 can define the eyelet 16, as shown in FIG. 4. The arm 36 can have the same or a smaller dimension or cross section than the opening or recess 32. In various other embodiments, the rotation base 34 can be connected to a region which sits proud with respect to the rotation base 34 and the arm 36 can snap fit, for example onto that region. As stated above herein, aligning the eyelet 16 with respect to the suture receiving openings 26 can form a continuous pathway through which the suture can freely slide. Rotating the eyelet 16 with respect to the suture receiving openings 26 on the first body 12 can cause the eyelet 16 and the suture receiving openings 26 to misalign and thereby enhance the securing of the suture by the twist.

The second body portion 14 can be contained partially in the first body opening or recess 32 or contained fully in the opening or recess 32. The second body portion 14 can also be oriented such that it lies substantially flush with the first body portion 12. Examples of substantially flush include fully coplanar or where the second body portion 14 terminates along the same plane as the terminal plane of the first body portion 12. Substantially flush also includes minor planar variance, such as where the second body portion 14 terminates with a slight (less than 10% of suture fixation apparatus total length) positive arcuate or other varying non-planar surface (ridges or a slot mated to a screw driver, for example) with respect to the first body portion 12, as depicted, for example, in FIG. 6A.

Figure 3:
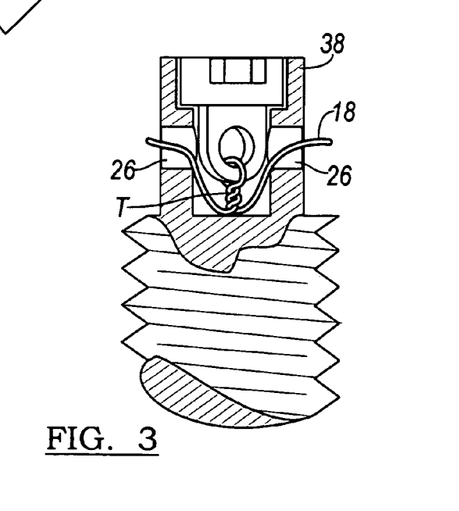
FIG. 3 depicts a frictionally engaged and self-twisted suture according to various embodiments.

The suture fixation apparatus can include a drive end 38 to receive a tool or driver. The drive end 38 is located at a proximal end of the first portion body 12, as shown in FIG. 3. The drive end 38 can be defined by a part of the first body portion 12 which extends equal to or proximal to the second body portion 14, as shown in FIGS. 4 and 6B, respectively. The drive end 38 can include a substantially hexagonal perimeter to be received within a substantially hexagonal socket or drive tool. As a further example, various features can be formed substantially on the end of the drive end 38 to be operated by a screw driver having a complimentary blade. The driver end 38 can be formed to facilitate advancement of the suture anchor by screwing, impacting, pushing, or combinations thereof, for example, or other suitable techniques.

Figure 5:
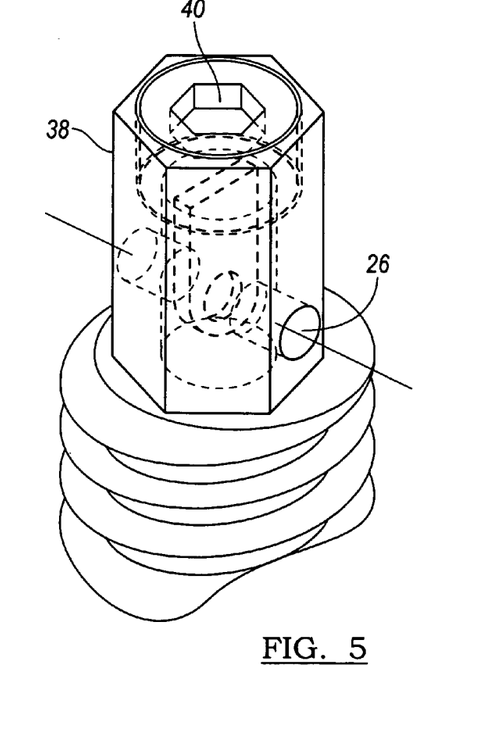
FIG. 5 depicts an assembled suture fixation device of FIG. 4.
Figure 6A:
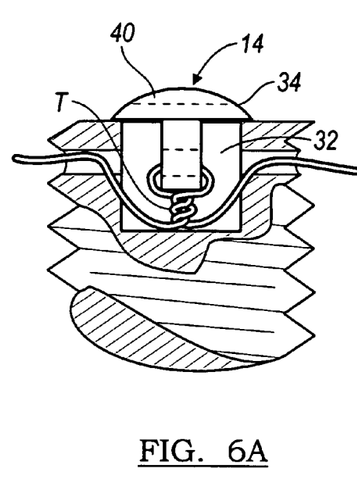
FIGS. 6A and 6B depict various tool engaging features for rotating the eyelet according to various embodiments.
Figure 6B:
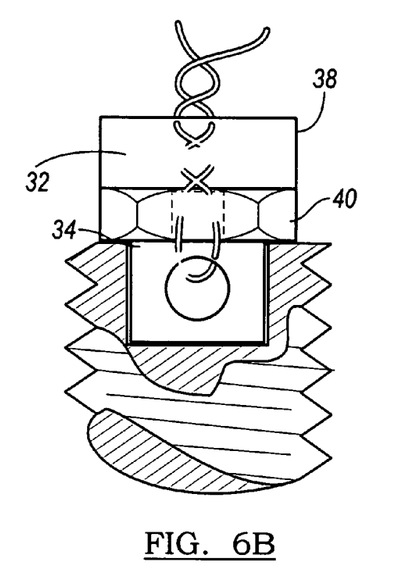

As best depicted in FIGS. 4, 5, 6A, and 6B, the second body portion 14 can be an integral part of the drive end 38. A tool engaging region 40 on the second body 14 can be formed to mate with a hex driver as shown in FIG. 5 or with a screw driver as shown in FIG. 6A. The tool engaging region 40 performs multiple functions including being adapted to facilitate insertion of the suture anchor 20 and/or adapted to facilitate rotation of the eyelet 16 to form the suture twist T.

In an exemplary use of the tool engaging region 40 in accords with FIGS. 4 and 5, a hex female driver is used to fit over the drive end 38 of the first body member 12 to advance the suture anchor 20 into a bony tissue. A male hex driver is inserted into the tool engaging region 40 to rotate the second body portion 14 and cause the suture 18 to wind on itself to form the twist T. It is appreciated that the hex female driver and the male hex driver can be formed as a single tool. For example, this exemplary driver is the mirror image of the drive end 38 and tool engaging region 40 as depicted in FIGS. 4 and 5. The tools, the drive ends 38, and a tool engaging regions 40, as described above can be modified to facilitate use of any suture fixation device 10 according to the present teachings.

The suture fixation device 10 can be made of a resorbable biocompatible material. The suture fixation device 10 can be formed of a polymer or a co-polymer, such as a co-polymer of polylactic acid and polyglycolic acid LACTOSORB as sold by Biomet, Inc. of Warsaw, Ind. Suitable polymers also include any other organic polymers (or co-polymers), such as polyethylene, polyetheretherketone (PEEK), and polyetherketoneketone (PEKK), as non-limiting examples. The suture fixation device 10 can be formed of a metal, such as titanium, stainless steel, or alloys of cobalt, chromium, etc.; a ceramic material; or any calcium-containing materials including, but not limited to monobasic, dibasic, and tribasic calcium phosphates and hydroxyapatite. The suture fixation device 10 can also be made of a composite of any of the above materials. Regardless of the selected materials, the suture fixation device 10 is formed such that it will have a selected pull-out strength to substantially hold the suture fixation device 10 in position after the device has been implanted into the bone.

Figure 8:
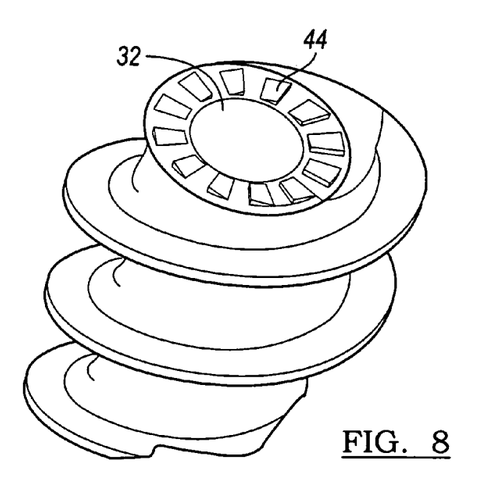
FIG. 8 depicts a top view of an anchor body with ratcheting elements and an opening to receive the rotatable eyelet and to produce a one-way rotation of the eyelet according to various embodiments.

Referring to FIGS. 1, 7, and 8, the suture fixation device 10 can include a ratcheting mechanism to provide one-directional movement of the second body portion 14 with respect to the first body portion 12. The ratcheting mechanism can include at least one ridge 42, located on one of the first body portion 12 or the second body portion 14 and a corresponding pawl 44 located on the other body portion. As shown, the ratcheting components are placed on the rotating base 34 of the second body 14 and the proximal end of the first body 12 which abuts the rotating base 34. The one-directional movement allows for additional turns to be placed on the twist T to prevent unintentional reduction in frictional force between the winds of the suture due to unwinding of the suture 18.

Figure 9A:
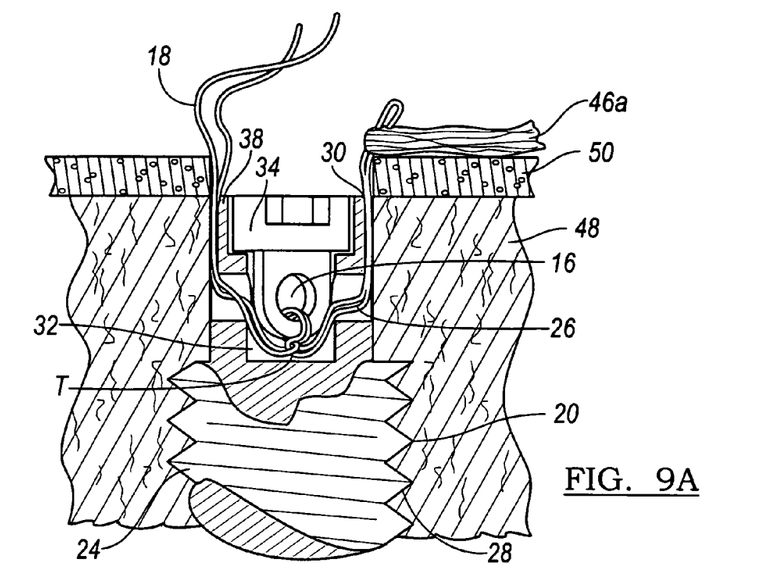
FIGS. 9A and 9B depict an environmental view of a suture fixation device according to various embodiments.
Figure 9B:
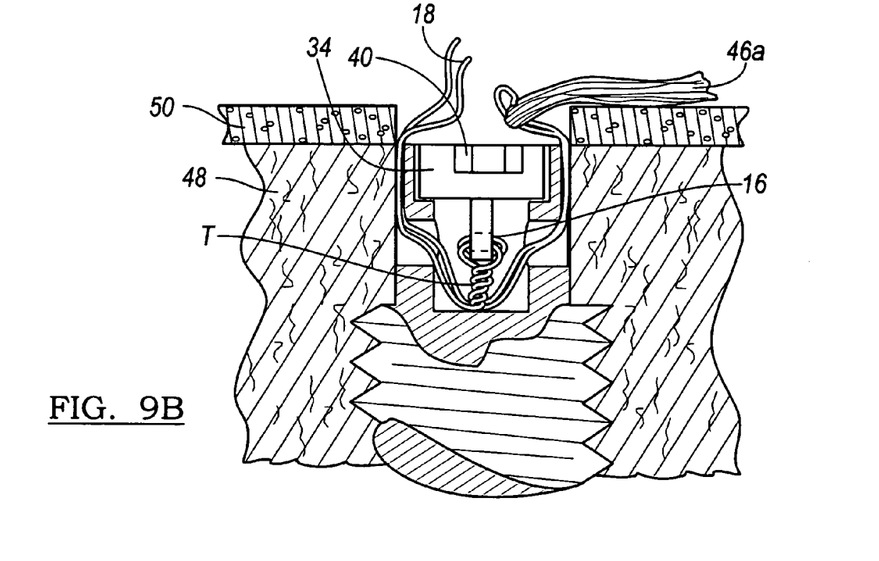

An exemplary use of the suture fixation device 10 is depicted in FIGS. 9A and 9B. The suture 18 is disposed in the eyelet 16 and through the suture receiving openings 26. In an embodiment where multiple suture receiving openings 26 are employed, a separate suture 18 or multiple suture strands are passed through the suture receiving openings 26 and the eyelet 16.

The suture fixation device 10 is placed into bone such that the first body portion 12 is fixedly attached to bone and does not rotate. The suture fixation device 10 can be placed into bone via the drive end 38 and a corresponding driver. Suitable placement techniques depend on the style of the suture fixation device or the bone engaging features of the suture fixation device 10 and can include, for example, threading the suture fixation device 10 into bone or impacting the suture fixation device 10 into a pre-formed opening in bone.

In various embodiments, the suture 18 is preloaded prior to placement of the suture fixation device 10 such that the suture 18 and the suture fixation device 10 are implanted in a single action or step. In other embodiments, the suture 18 can be loaded in the eyelet 16 after the suture fixation device 10 has been placed in the bone.

Once the first body portion 12 is fixedly attached and the suture 18 is placed, the second body portion 14 is engaged through the rotation base 34 and/or tool engaging region 40. Engagement of the rotation base 34 and/or the tool engaging region 40 can be achieved using the driver or a specially adapted tool. The rotation base 34 is rotated in a single direction to cause the suture 18 to wind upon itself to form the twist T. The folds of the twist T provide friction between the strand and cause the suture 18 to lock upon itself and prevents the unintentional removal of the suture 18 from within the suture fixation device 10. In various embodiments the suture 18 is secured by rotating the rotation base 34 at least 10 times to cause 10 turns of the suture 18. The suture 18 can also be secured by as few as 2 twists, as many as 25, 250, or 1,000, etc. twists, or any suitable number of twists as needed. The twisting can be achieved manually as the surgeon's hands rotate the rotation base 34. In embodiments requiring a higher number of twists, a tool having a rotation amplifying gear or mechanism can be used to turn a single manual rotation into multiple twists.

In embodiments having the ratcheting mechanism, the rotation base 34 is rotated in a single direction to cause the suture 18 to wind upon itself and form the twist T. In the example as described above, the ridges 42 of the first body portion and the pawls 44 on the second body portion pass each other thereby causing additional passes of the twist T and subsequently tightening the twist T and thereby securing the suture 18.

The suture fixation device 10 can be advantageously used to finely tighten a tissue 46. The suture 18 is looped through the tissue and through the eyelet 16 and suture openings 26. A folded loop is generally through the tissue and the free ends of the suture loop extend out of the hole in bone. The free ends of the suture 18 are held tightly (by hand or with any suitable surgical device) and the suture fixation device 10 is rotated to tighten the suture 18 and secure the tissue 46 in or adjacent to the opening in bone.

Figure 10:
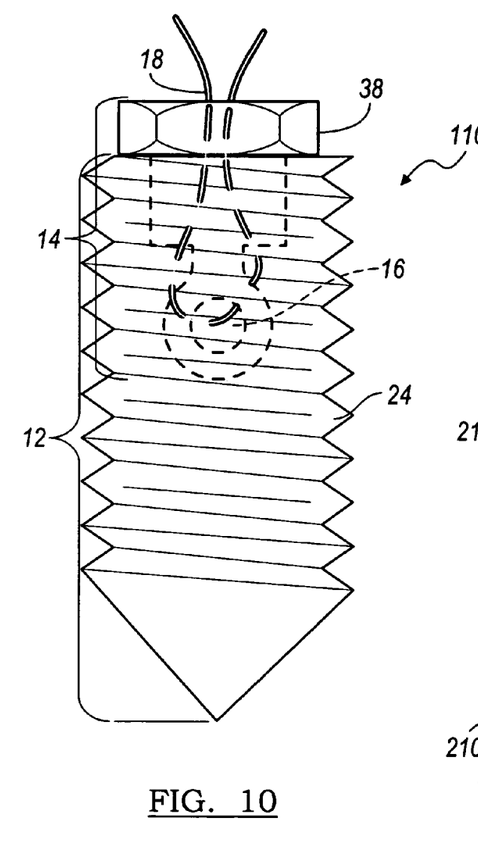
FIG. 10 depicts a suture fixation device having a recessed rotatable eyelet according to various embodiments.

Referring to FIG. 10, a suture fixation device 110 is provided that is substantially similar to the suture fixation device 10. The suture fixation device 110 includes a first body portion 12, a second body portion 14, and an eyelet 16. The suture fixation device 110 is adapted such that the second body portion 14 begins within the anchor body shaft 24 and terminates prior to the proximal end of the anchor body shaft 24. The eyelet 16 is completely contained in the first body portion 12. The free ends of the suture 18 extend outwards from the drive end 38 instead of through suture openings 26 and are guided through the suture receiving channel 30. The suture fixation device 110 can be made of the same materials as those described above and can be used with similar surgical techniques. The suture fixation device 110 can also include any of the drive ends 38 and/or 40 for either the eyelet 16 or the first anchor body 12, as detailed in earlier embodiments.

Referring to FIGS. 11 through 16, a suture fixation device 210 is provided. The suture fixation device 210 includes a first body portion 212 and a second body portion 214. The suture 18 is secured with respect to the tissue when the first body portion 212 and the second body portion 214 are positioned to trap the suture therebetween, as detailed below.

Figure 11:
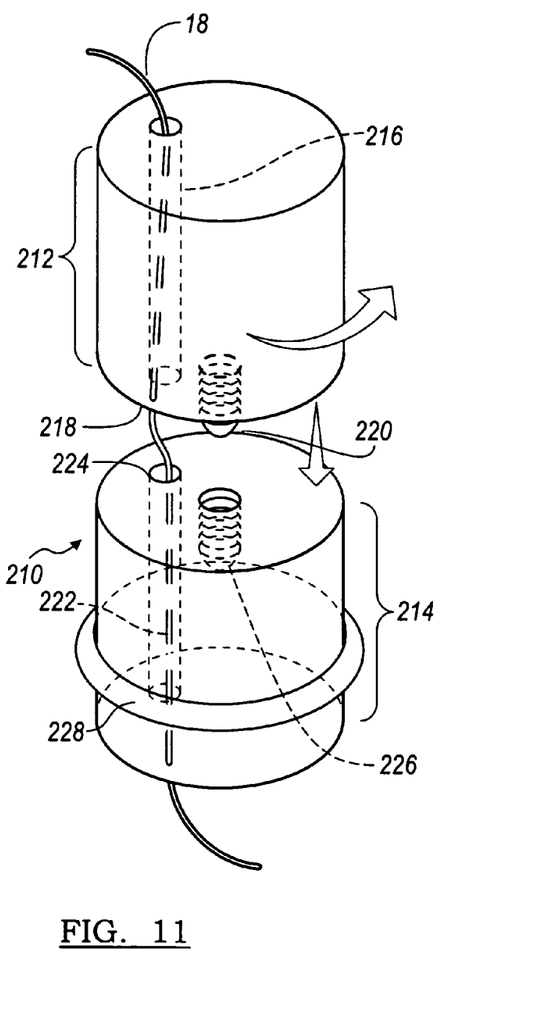
FIG. 11 depicts a suture fixation device in an open position according to various embodiments.

The first body portion 212 includes a first body channel 216. The first body channel 216 can be at the central axis of the first body portion 212 or at an offset axis, as shown. The first body portion 212 includes a first mating surface 218 and a first mateable threaded region 220. The first mateable threaded region 220 is offset from the first body channel 216. The first mateable threaded region 220 can be located at the central axis of the first body portion 212.

The second body portion 214 includes a second body channel 222 having a common longitudinal axis to the first body channel 216. The second body portion 214 includes a second mating surface 224. The second mating surface 224 further comprises a mateable threaded region 226 that is adapted to mate with the first mateable threaded region 220. The second mateable threaded region 226 is offset from the second body channel 222. The second meteable threaded region 226 can be located at the central axis of the second body portion 214.

Figure 15:
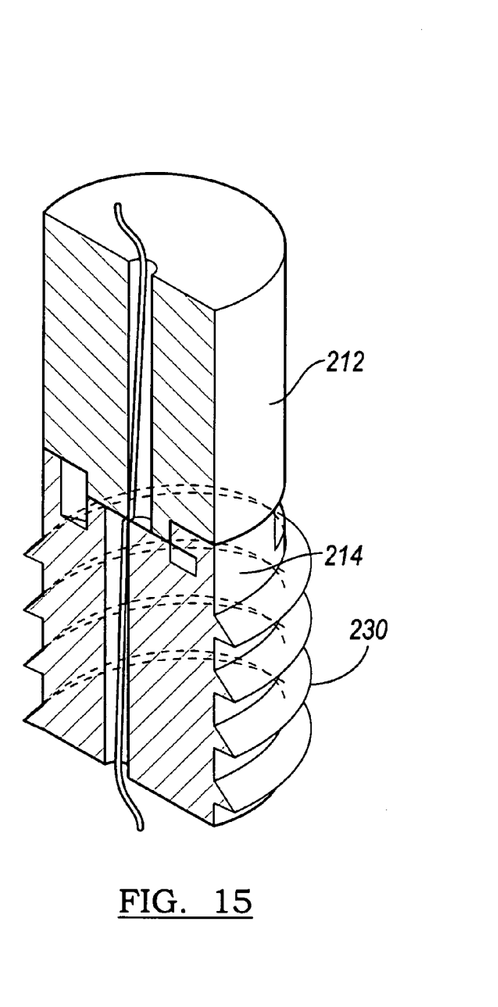
FIG. 15 depicts a suture fixation device with a twist lock in the fully deployed position according to various embodiments.

The second body portion 214 also includes a bone engaging attachment feature 228. The bone engaging attachment feature can be a ridge 228, for example, as depicted in FIG. 11 or the attachment feature(s) can be threads 230 as depicted in FIG. 15. The attachment features can also includes one or several of a spike, pin, ridge, tooth, or another bone engaging element to fixedly hold the fixation device 210.

The first body portion 212 and the second body portion 214 and subcomponents are substantially rigid and non-flexible. The first body portion 212 and the second body portion 214 and subcomponents thereof can be made of any of the materials detailed above.

The first body portion 212 and the second body portion 214 can be moved relative to each other. In a first or open position, the channels 216, 222 of the first body portion 212 and the second body portion 214 are in communication and aligned along the same axis. A suture 18 freely passes through the first body portion 212 and the second body portion 214 through the continuous pathway.

Figures 12, 13:
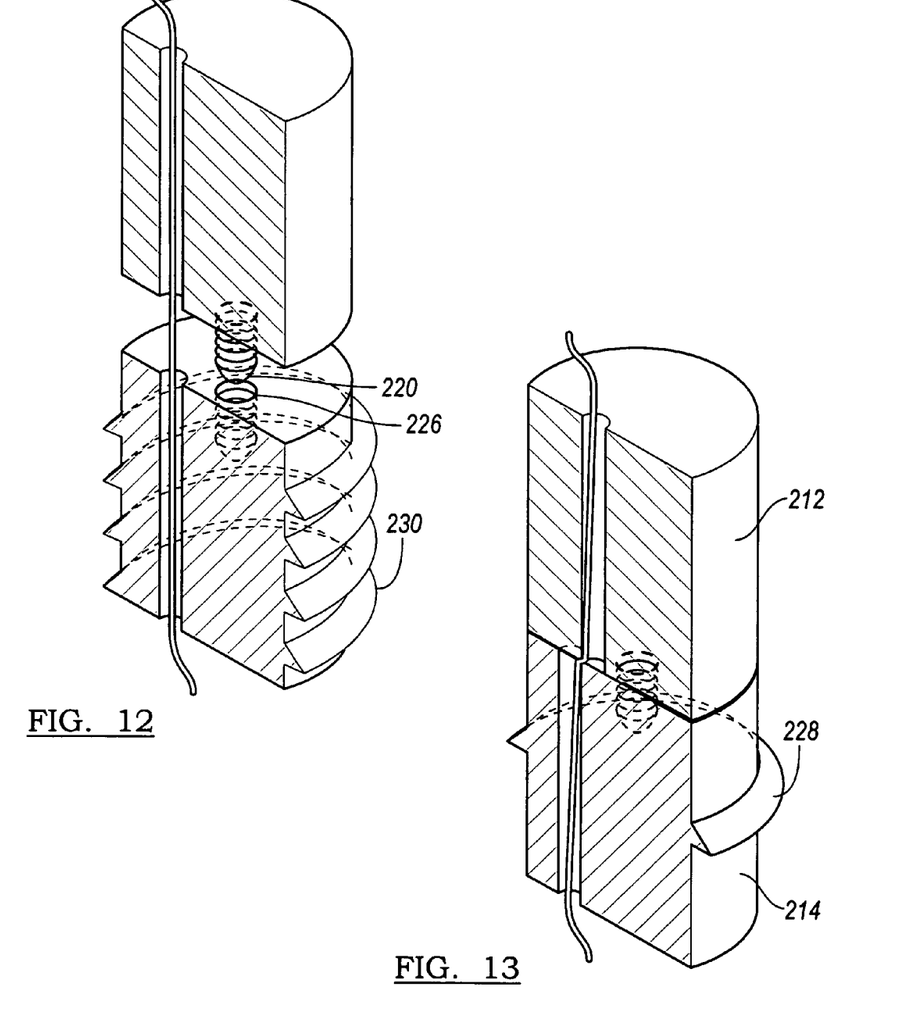
FIG. 12 depicts a cut away view of a suture fixation device in a partially deployed position according to various embodiments.
FIG. 13 depicts a cut away view of a suture fixation device in the fully deployed position according to various embodiments.

In a second position, one channel in either the first body portion 212 or the second body portion 214 is moved out of communication with the other channel such that channels 216, 222 are not aligned along the same axis. This second position can be a misaligned position or the fully deployed final position where the first body portion 212 and the second body portion 214 are mateably locked together. When the channel 216 components are misaligned and the first body portion 212 and the second body portion 214 are connected and the suture 18 becomes locked between the two body portions to prevent unintentional advancement or dislodging of the suture 18.

In use, the first body portion 212 and the second body portion 214 are oriented such that the first body mating surface 218 and the second mating surface 224 are facing each other. The first body channel 216 and the second body channel 222 are aligned to share the same longitudinal axis and allow for passage of a suture therebetween. The suture 18 is loaded in the fixation device 210 such that it passes through both the first body portion 212 and the second body portion 214.

The first body mateable threaded region 220 and the second body mateable threaded region 226 are then brought into contact. The first body mateable threaded region 220 and the second body mateable threaded region 226 are engaged by rotating the first body with respect to the second body to cause the first body 212 and second body 214 to move in closer proximity, as indicated by the arrows. As the mateable threaded regions mate and the first body portion 212 is moved with respect to the second body portion 214, the first channel and the second channel no longer share the common starting or first position axis. Subsequently, the first body channel 216 and the second body channel 222 no longer share the same axis. This causes the suture 18 to become partially lodged between the first mating surface 218 and the second mating surface 224 as the first body portion 212 and a second body portion 214 are brought into the deployed or closed position.

Figure 16:
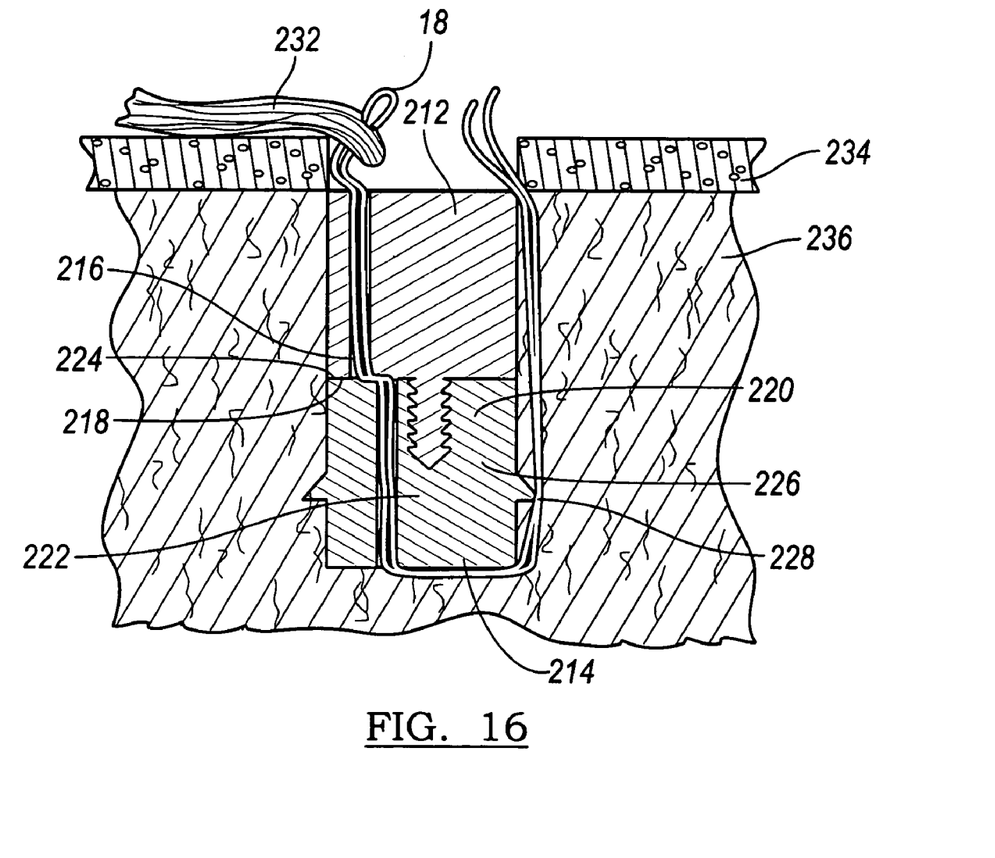
FIG. 16 depicts an environmental view of a suture fixation device according to various embodiments.

The suture 18 is sewn into tissue 232, for example a natural ligament or a graft for ACL or MCL repair. The suture fixation device 210 is then loaded into a pre-formed opening in bone. A suture loop can be passed through the tissue 232, the suture fixation device 210, and out of the opening in bone such that free ends of the suture are outside of the opening in bone as detailed earlier herein. The bone engaging features 228 or 230 fixedly attach the suture fixation device 210 to the opening in bone. Rotating the first body portion 212 with respect to the fixed second body portion 214 causes the suture to become locked between the first body portion 212 and the second body portion 214 and thereby secures the suture with the tissue 232, the underlying bone 234, and/or adjacent soft tissue 236, such as cartilage. It is understood that the suturing, fixation device loading, and fixation device 210 body rotating can be performed in any order and the order listed here is merely exemplary.

Figure 14:
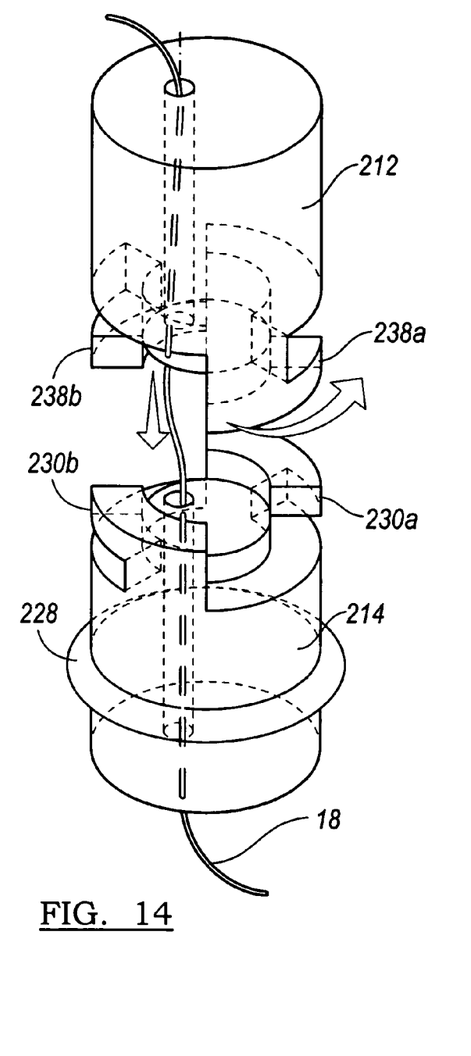
FIG. 14 depicts a suture fixation device with a twist lock according to various embodiments.

Referring to FIGS. 14 and 15, the suture fixation device 210 includes arms 238a and 238b on the first body portion 212 and corresponding arms 230a and 230b on the second body portion 214. The arms 238a, 238b are oriented with arms 230a, and 230b such that a single twist of the suture fixation device 210 causes the channels 216 and 222 to become misaligned and thereby trapping the suture 18 between the first body portion 212 and the second body portion 214.

The suture fixation devices of the present teachings are useful to secure a suture or sutures to a defect site. The methods are useful for a variety of soft tissue repairs including, but not limited to, labral repairs, glenoid repairs, and medial collateral ligament repairs. Any of the suture fixation devices detailed above can be used in conjunction with the methods.

A suture 18 is passed through a rotatable region of a suture fixation apparatus. For example, the suture 18 can be passed through the eyelet 16 of the suture fixation devices 10 and 110. With respect to the suture fixation device 210, the suture 18 can be passed through either the first body portion 212 or the second body portion 214 as both body portions rotate with respect to each other.

The suture fixation device 10, 110, or 210 is then fixed to a bony tissue 48, 236 to prevent movement of a region of the fixation device. The fixation is achieved by using the bone engaging attachment features 28, 228, and/or 230 as detailed earlier herein. The rotatable region containing the suture is rotated to form a twist in the suture to frictionally secure the suture.

The description of the present teachings is merely exemplary in nature and, thus, variations that do not depart from the gist of the present teachings are intended to be within the scope of the present teachings. Such variations are not to be regarded as a departure from the spirit and scope of the present teachings.

What is claimed is:

1. A suture anchor, comprising:
    a first body portion defining a recess at a proximal end, a suture receiving channel transverse to the recess, and a bone engaging feature at a distal end to fixedly engage a bony tissue;
    a second body portion defining an eyelet for receipt of a suture where engaging the second body portion rotates the eyelet with respect to the first body portion; and
    a rotational ratcheting device to provide only one-directional rotational movement of the second body portion with respect to the first body portion;
    wherein rotation of the second body portion causes the suture to form a twist to frictionally secure the suture;
    wherein the recess provides a clearance to receive the twist below the eyelet between a distal end of the second body portion adjacent the eyelet and a bottom of the recess when the suture receiving channel and the eyelet are positioned in the same plane.

2. The suture anchor according to claim 1, wherein the second body portion is located at a proximal end of the suture anchor.

3. The suture anchor according to claim 1, wherein the second body portion is at least partially contained in the recess.

4. The suture anchor according to claim 1, wherein the second body portion is fully contained in the recess.

5. The suture anchor according to claim 1, wherein the second body portion is contained in the recess such that a proximal end of the second body portion and a proximal end of the first body portion are substantially flush.

6. The suture anchor according to claim 1, wherein the suture anchor comprises a drive end to receive a driver and advance the suture anchor by a technique selected from the group consisting of: impacting, screwing, pushing, and combinations thereof.

7. The suture anchor according to claim 1, wherein the ratcheting mechanism comprises at least one ridge located on one of the first body portion and said second body portion and at least one pawl disposed opposite the ridge located on the other of the first body portion and the second body portion.

8. The suture anchor according to claim 7, further comprising a plurality of ridges and a plurality of pawls.

9. The suture anchor according to claim 1, wherein the suture receiving channel is in communication with the eyelet of the second body portion, and further wherein the eyelet and the suture receiving channel align to form a continuous linear passage that extends through the first body portion and the second body portion.

10. A suture anchor comprising:
    a first body portion defining a recess at a proximal end and having a first suture receiving channel; and
    a second body portion having a second suture receiving channel;
    wherein the first suture receiving channel and the second suture receiving channel have an aligned position to provide a continuous passage for movement of a suture therebetween and at least one of the first suture receiving channel and the second suture receiving channel is adapted to be rotated relative to the other into a deployed position to misalign the first suture receiving channel and the second suture receiving channel to prevent movement of the suture therebetween, the continuous passage being aligned along the transverse axis of he suture anchor;
    wherein the relative rotation causes the suture to form a twist below the second suture receiving channel in a clearance provided by the recess between a distal end of the second body portion adjacent the second suture receiving channel and a bottom of the recess when the first and second suture receiving channels are positioned in the same plane.

11. The suture anchor according to claim 10, further comprising an interface wherein a first mating surface of the first body portion engages a second mating surface of the second body portion.

12. The suture anchor according to claim 10, wherein the second suture receiving channel comprises an eyelet.

13. A suture anchor comprising:
    a threaded suture anchor body having a bone engaging surface feature to fixedly engage a bony tissue where the suture anchor body has a proximal end defining a recess and a suture receiving channel communicating with the recess, and a distal end;
    a rotatable base having an eyelet where the rotatable base and the eyelet are located in the recess of the threaded suture anchor body and are distal to the suture anchor body proximal end; and
    a rotational ratcheting device to provide only one-directional rotational movement of the threaded suture anchor body with respect to the rotatable base;
    wherein rotation of the rotatable base causes the suture to form a twist to frictionally secure the suture;
    wherein the recess provides clearance to receive the twist below the eyelet between a distal end of the rotatable base adjacent the eyelet and a bottom of the recess when the eyelet and the suture receiving channel are positioned in the same plane.

14. The suture anchor of claim 8, wherein the ridges are located on a planar mating surface of the first body portion and the pawls are located on a planar mating surface of he second body portion.

15. The suture anchor of claim 1, wherein the second body portion comprises a recessed driver-receiving portion at a first end and the eyelet is at a second end opposite the first end.

16. The suture anchor of claim 10, wherein the second body portion comprises a recessed driver-receiving portion at a first end and the eyelet is at a second end opposite the first end.

17. The suture anchor of claim 11, wherein the first mating surface is planar and comprises ridges and the second mating surface is planar and comprises pawls to provide a ratcheting device.

18. The suture anchor of claim 17, wherein the ratcheting device provides rotational movement of the first body portion with respect to the second body portion in only one-direction.

* * * * *

UNITED STATES PATENT AND TRADEMARK OFFICE
CERTIFICATE OF CORRECTION

PATENT NO. : 7,674,276 B2
APPLICATION NO. : 11/545036
DATED : March 9, 2010
INVENTOR(S) : Kevin T. Stone et al.

It is certified that error appears in the above-identified patent and that said Letters Patent is hereby corrected as shown below:

In the Claims:

Column 10, Line 33, Claim 13, --he-- should be "the."

Signed and Sealed this
Fourteenth Day of May, 2013

Teresa Stanek Rea
*Acting Director of the United States Patent and Trademark Office*